United States Patent [19] [11] 3,993,078
Bergentz et al. [45] Nov. 23, 1976

[54] INSERT FOR USE PREFERABLY IN VASCULAR SURGERY

[75] Inventors: Sven Erik Bergentz; Kurt Sven Theodore Strid, both of Malmo, Sweden

[73] Assignee: Gambro AG, Switzerland

[22] Filed: Nov. 3, 1975

[21] Appl. No.: 628,070

[30] Foreign Application Priority Data
Nov. 4, 1974 Sweden.............................. 7413811

[52] U.S. Cl. .................................. 128/334 R; 3/1; 3/1.4
[51] Int. Cl.² ....................................... A61B 17/04
[58] Field of Search ............ 128/1 R, 334 R, 334 C; 128/335; 3/1, 1.4

[56] References Cited
UNITED STATES PATENTS
3,562,820  2/1971  Braun ....................... 3/1.4
3,833,940  9/1974  Hartenbach ................. 3/1
3,842,441  10/1974  Kaiser ........................ 3/1
3,882,845  5/1975  Bucalo ........................ 128/1 R Primary Examiner—Edgar S. Burr
Assistant Examiner—Paul T. Sewell
Attorney, Agent, or Firm—Lerner, David, Littenberg & Samuel

[57] ABSTRACT

An insert for use preferably in vascular surgery which includes an unperforated, hollow body of substantially circular cross-section. The body is provided with a spiral line of fracture extending about the periphery of the body and defining continuous spiral coils to thereby weaken the cohesion of the body along the spiral coils so that the body may be disassembled into an elongated thread having a substantially smaller cross-section than that of the insert.

10 Claims, 8 Drawing Figures

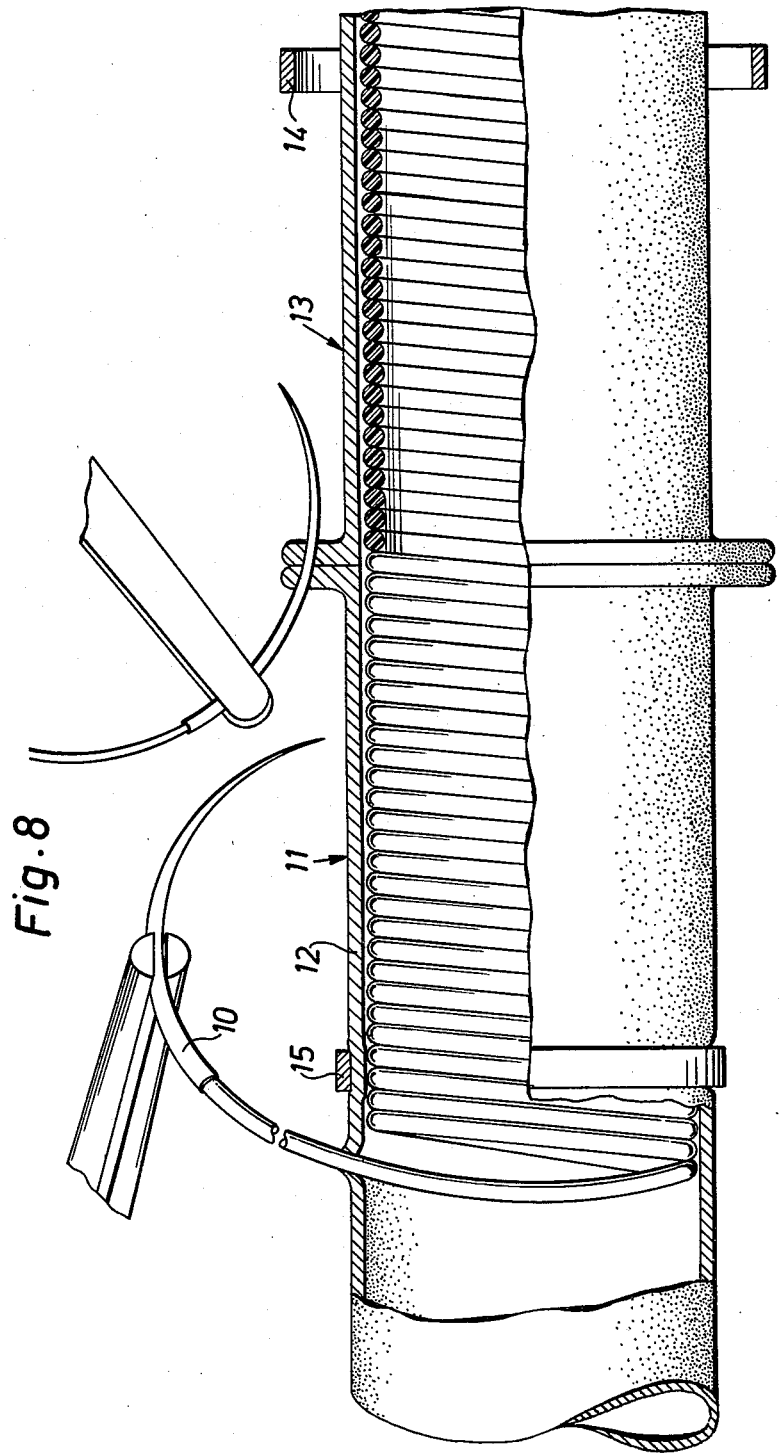

INSERT FOR USE PREFERABLY IN VASCULAR SURGERY

BACKGROUND OF THE INVENTION

In medicine, and most particularly in the field of vascular surgery, it is often necessary to operate on vessels, for example, for the removal of calcifications from blood vessels. In making such operations, it is necessary to arrest temporarily the blood circulation through the part of the blood vessel to be treated. Normally the operation is effected in that the blood vessel is constricted by means of Péan's forceps on either side of the region to be treated, the blood vessel being then opened or cut off at the treatment region. The treatment proper is then carried out and when this is terminated the incision surfaces of the blood vessel are sutured with, for example, catgut. In order to minimize the risks associated with the arrest of the blood circulation through the vessel (hemostasis) it is important that the operation be carried out as rapidly as possible, normally within 10–15 minutes. Furthermore, the arrest of the circulation often cuts off the blood supply to important organs, such as the brain in, for example the treatment or so-called "de-coking" of the carotid artery. In this treatment, it is required that the blood circulation to the brain be cut off for at most 1–2 minutes if permanent brain damage is to be avoided. It will be appreciated that it is extremely difficult to carry out an operation of the above-mentioned type in such a short time. In order, in such cases, to give the surgeon longer time in which to work, a method has been developed according to which the carotid artery is first constricted on either side of the treatment region. A longitudinal slit is then made at the treatment region, instead of cutting off the carotid artery, as is normally the case with other blood vessels. A plastic tube is then inserted into the longitudinal slit and is disposed so that it extends beyond both ends of the slit. The artery is then fixedly clamped against the plastics tube near its ends, whereupon the constriction on either side of the treatment region is removed. As a result, a free passage for the blood circulation will be obtained at the same time as the part of the carotid artery to be treated or "de-coked" is exposed so that the surgeon is given a reasonable period of time to carry out the treatment. When the treatment has been completed, the plastic tube must be removed and the blood vessel closed. To this end the artery is once again constricted on either side of the treatment region, the forceps on the artery at the ends of the plastic tube are released, the plastic tube is taken out, the slit in the artery is sutured and finally the constriction on either side of the treatment region is removed.

Even if the above-described procedure entails substantial progress as compared with conventional surgery, it should nevertheless be observed that both the first stage with the insertion of the plastic tube and the final stage with the removal of the plastic tube and the suturing of the artery must be effected within the given time limit of 1–2 min., preferably within 1 min. Here, the initial stage is relatively rapid and offers no great problem as regards time, whereas the final stage which includes the suturing of the artery is much more time-consuming and difficult to carry out within the given period of time. The present invention obviates this problem in that the constriction of the blood circulation need only be effected in the initial stage, whereas the final stage can be carried out with uninterrupted blood circulation, that is to say the surgeon can work without being pressed for time.

In another known type of operation, a damaged part of a blood vessel is removed and replaced with an artificial graft in the form of a tube of knitted fabric manufactured from "DACRON" (polyethylene terephthalate). The graft includes a support portion which is removed once the graft has been united permanently, by healing up, to the blood vessel. This removal is effected by a further operation approximately a couple of months after the first operation when the graft was inserted. As will be explained in greater detail below, the present invention makes it possible to remove the support portion without any special operation. It will be readily observed that this entails considerable advantages.

A further type of operation in ureteritis involves the removal of a portion of the ureter, the remaining portions of the ureter being sewn together. A flexible insert of rubber is, in this case, inserted into the ureter, the element bridging the region of the suture and preventing urine from coming into contact with said region, thereby facilitating healing. However, after the healing process, the insert element must be removed, which entails a new operation. The present invention also obviates the need in this case of a subsequent operation and permits instead the removal of the insert without any special surgical procedure.

These and further advantages gained by the present invention are achieved in that the tubular insert is designed such that, when necessary, it can be divided or taken apart along a previously provided line of fracture to form a thread of a substantially smaller cross-section than that of the insert. According to the invention, the insert consists of an unperforated hollow body of substantially circular cross-section and having a spiral line of fracture running about the periphery of the body and weakening the cohesion of the body at the spiral coils for parting of the body as an elongated thread. Further characteristic features of the invention will be apparent from the appended claims.

The nature of the invention and its objects will be more fully understood from the following description of the drawings, and discussion relating thereto.

In the accompanying drawings:

FIG. 8 shows the use of the insert in a vascular surgical operation.

DETAILED DESCRIPTION

Figure 1:
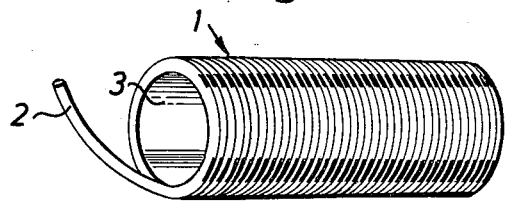
FIG. 1 is a schematic perspective view of an insert according to the present invention.

The insert 1 shown in FIG. 1 consists of a hollow cylindrical body which is formed by a spirally wound thread 2. The spirally wound thread coils are held together by a binder 3, as is more clearly apparent from FIGS. 3–5. The binder 3 is substantially provided on the inner side of the cylindrical body and there forms a smooth inner surface 4 (see FIGS. 3–5), whereas the outer side is uneven and is formed by the spirally wound thread coils and the groove 5 running between them.

Figure 2:
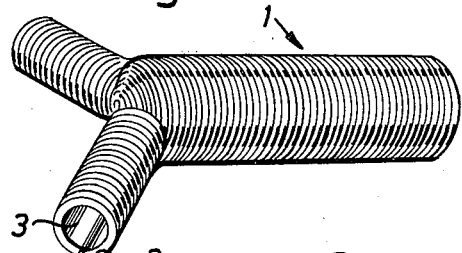
FIG. 2 is a schematic perspective view of another embodiment of the invention.

FIG. 2 illustrates an embodiment of the insert of FIG. 1, this embodiment in principle comprising three inserts according to FIG. 1 combined to form a Y-tube. In this instance, two of the three tube branches are constructed in the same way as the insert of FIG. 1, whereas the third branch, for example, the thick major branch, is formed in that the threads from both of the other branches are each wound parallel to each other in a spiral. The third branch, in its capacity as the thick major branch, will thus display two thread ends at its free end.

Figure 3:
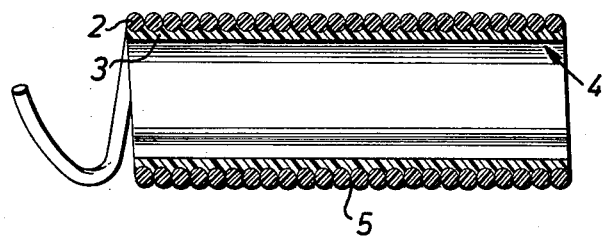
FIG. 3 is a longitudinal section through the insert according to FIG. 1 and shows the construction of the insert.
Figure 4:
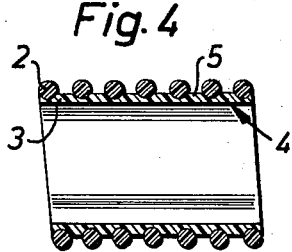
FIGS. 4–7 show alternative designs of the insert.

The embodiment shown in FIG. 4 differs from that in FIG. 3 in that the thread 2 has not been wound in tight coils but with a certain spacing between the thread coils.

Figure 5:
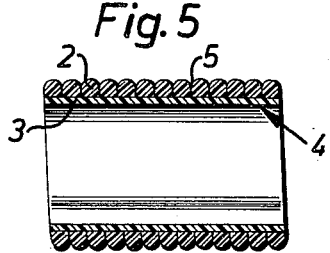

The embodiment shown in FIG. 5 differs from that in FIG. 3 in that the inner side of the spirally-wound thread 2 has been flattened thereby contributing to a smoother inner surface of the insert.

Figure 6:
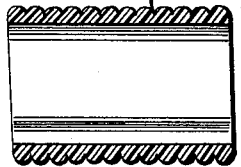

FIG. 6 illustrates a special construction of the insert according to the invention. Unlike the earlier-mentioned inserts this construction does not comprise a spirally-wound thread which is connected by means of a binder. Instead, it consists of a single cylindrical insert which by lathe-turning or in some other way, is provided with a groove 5 which runs in a spiral about the circumference of the insert. The inner surface of the insert is smooth, as in the insert according to FIG. 1.

The insert according to FIG. 6 is preferably obtained from a hose of elastic polymer material such as silicone rubber which, by lathe-turning with a cutting tool in the manner described below, is provided with a spiral groove 5. The groove 5 is illustrated in the form of a groove which is flared outwardly, that is to say, the outer side of the insert is bumpy. However, it will be appreciated that the groove 5 can of course be in the form of a straight notch so that the outer side of the insert will remain substantially flat and smooth. Furthermore, in FIG. 6 the insert has been shown in the form of a homogeneous body of a single material, but if necessary or desirable, a reinforcement thread, for example, of metal may be cast into the hose body, the reinforcement thread being so disposed that, when the groove 5 is created, it will lie between the spirally running groove coils and will thus, when the insert is taken apart, constitute a reinforcement located centrally in the resultant thread.

Figure 7:
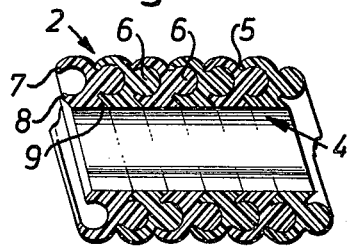

FIG. 7 shows another special construction of the insert according to the invention, this construction not including any binder, the spirally wound thread coil being instead held together by the particular design of the thread 2. This generally entails that the thread body is provided on its one side with projecting elastic jaws 7, 8 which are intended to surround and, by snap-action, retain a corresponding adjacent thread body as shown in FIG. 7. In this instance, the lower side of one of the jaws is smooth in order to give the finished insert a smooth inner surface 4. In order to create further cohesion of the finished insert, the smooth jaw 8 can, at its fixing point in the thread body, have an additional smaller jaw 9, as is also apparent from FIG. 7. It will be understood that the described embodiment according to the invention is not restricted to the configuration shown in FIG. 7 but may be modified in several ways within the spirit and scope of the invention, the thread being shaped in accordance with the tongue and groove principle. However, care should be taken to ensure that the construction is such that no air pockets occur in the finished insert which could involve risks in its surgical use.

A distinguishing feature of all of the above-described inserts according to the invention is that in normal handling they retain their solid form and integrity but that they can simply be divided or taken apart as a thread by pulling at the free thread end at each of the both ends of the insert. This thread is, to be more precise, the thread from which the insert was originally wound. The insert shown in FIG. 2 is divided or taken apart by simultaneous pulling at the free thread ends of the tube branches which were wound with only one thread. In order that the insert be kept intact during normal handling, the cohesive binder 3 must be strong and at the same time elastic, since handling can in many cases be relatively incautious and can include radial pressure (both inwardly and outwardly) against the insert, axial and radial compression of the insert and even a certain axial stretching of the insert. However, the insert should not be too easily compressible in a radial direction, but must essentially retain its original cylindrical form under the prevailing conditions. Examples of suitable materials for the thread 2 are: polyethylene, polyvinyl, polytetrafluoroethylene and DACRON. An at present particularly preferred material for the thread 2 consists of a core of metallic material such as, for example, copper coated with a polymer material. Examples of suitable materials for the binder are: film-forming latexes of different types, the latex preferred at present being Neopren 400 which is a rubber latex available from Chematex, Malmo, Sweden. In order to create the best adhesion between the thread and binder, the materials in these two articles should be similar; for example, if the binder comprises the above-mentioned latex, the thread can comprise a copper core coated with a layer of the same latex. Furthermore, in view of the preferably medicinal use of the invention, both the thread and the film-forming binder should comprise materials which do not give rise to tissue reactivity. However, it should be emphasized that the invention is not bound to any special material, every material which satisfies the above-mentioned requirements being usable both for the thread 2 and for the film-forming binder 3.

In the above-described pulling of the free thread end, the groove 5 between the thread coils serves as a line of fracture along which the insert parts. On this point it is important from the medicinal point of view that the film-forming binder parts along the line of fracture in a clean and elegant manner without the formation of loose flakes of binder.

In the embodiments shown in FIGS. 6 and 7 the spirally running groove 5 also serves as a line of fracture on the parting of the insert by pulling at the free "thread" end, that is to say the insert parts along the groove 5. However, in this case there is no film-forming binder to part or break, the parting being effected in FIG. 6 in the material of the insert proper, because of the weakening occasioned by the groove 5. In FIG. 7 this weakening results from the opening of the snap-action joint, that is to say the removal of the thread body 6 from the retaining jaws 7, 8.

The insert according to the invention shown in FIGS. 3-5 in the drawings is produced first by the application on a support, such as a mandrel, of a layer of the film-forming binder. This is suitably effected by dipping the mandrel one or more times in a latex solution until a binder layer of the desired thickness is obtained. A thread is then wound in spiral around the mandrel and on the film-forming binder so that that portion of the thread which is facing the mandrel will be at least partially embedded in the binder. The mandrel with the assembly disposed thereon is then exposed to heat treatment by, for example, the blow-on of hot air to bake the thread and the binder together to a single unit. When the insert is finished it is removed from the mandrel by the blowing in of air between the surface of the mandrel and the inner surface of the insert, this being effected through channels or slots disposed in the mandrel. As a result of the blowing in of air, the insert loosens from the mandrel and can easily be drawn off from the mandrel. Of course, it is also possible, before the manufacture of the insert, to coat the surface of the mandrel with a mould release agent thereby making possible the removal of the finished insert. When the insert is being wound, the thread can be wound such that the thread coils are disposed immediately adjacent one another, but it is preferable to wind the thread coils with a slight spacing, as shown in FIG. 4, in order to avoid the drawing up of the subjacent binder, by capillary action, between the thread coils which results in an increased binding surface, thereby providing an insert which requires unsuitably high parting force. If the winding of the insert is effected manually, the spacing between the thread coils can be achieved by winding, simultaneously with the thread intended for the insert, a second thread whose diameter corresponds to the desired spacing. This second thread has low affinity to the binder and is removed after the completion of the winding. When the thread is being wound by machine, the desired spacing is simply obtained by adjustment of the desired pitch of the machine. It will be appreciated that the insert can also be composed of two or more parallel-wound threads, but this construction is less preferable because of the disadvantages inherent in the parting of the insert in that pulling must be effected at more than one thread end. In the case where an insert of the configuration illustrated in FIG. 5 is to be produced, one side of the thread is chamfered by grinding or in some other way immediately before the winding of the thread on the mandrel. It may also be advisable, in conjunction with this chamfering, to provide the chamfered face with a radially inwardly directed groove which, as the thread is wound, serves as a receptacle space for excess binder which would otherwise creep up between the thread coils and cause increased binding surface and thereby increased parting force.

As was intimated earlier, the embodiment illustrated in FIG. 6 is manufactured from a hose blank of, for example, silicone rubber. As starting materials, hoses with different dimensions are used depending on the desired dimension of the finished insert, it being possible for the outer diameter generally to vary between 2 and 10 mm and the inner diameter between 1 and 8 mm. The hose blank is clipped into pieces of a suitable length, for example 4–6 cm, these lengths being then applied to a mandrel of a slightly larger diameter (for example, 4 mm) than the inner diameter of the hose, and passed onto the mandrel in that the hose lengths are expanded by means of compressed air applied through a nozzle. The mandrel is rotatably mounted on a lathe and when the hose length is in place, the mandrel and the hose length are rotated at, for example, 300–400 rpm. The line of fracture or groove 5 is then created by passing a razor blade tool formed as a cutting tool along the hose length at an adapted speed, so that a groove 5 of the desired pitch is obtained. The pitch can be adapted such that, when the insert is parted, the resultant thread will have a cross-section of approximately 1 mm$^2$. A suitable cutting depth for the cutting tool has been found to be a depth which creates a material thickness of approximately 0.15 mm between the bottom of the groove 5 and the mandrel. When the hose length on the mandrel is provided with the spirally running groove, the thus formed insert is removed from the mandrel and one end of the insert is parted so that a thread end is obtained on which is fixed a suture needle, whereupon the insert with the suture needle is packed sterile in a known manner. It should be observed that the above-indicated measurements and dimensions are illustrative and not restrictive.

The embodiment shown in FIG. 7 is suitably produced by extrusion of a thread of the desired cross-sectional contour and, in direct conjunction therewith, spirally winding the thread and joining the juxtaposed thread coils by the above-described snap-action.

The diameter of the thread and the thickness of the binder layer employed are dependent upon intended use of the insert, that is to say, the cross-section of the blood vessel to be treated, the desired parting force for the insert, the material of the binder layer etc. Generally, the diameter of the thread is preferably approximately 0.2–0.8 mm and the thickness of the film-forming binder layer is approximately 0.02–0.05 mm. The finished insert should preferably have a diameter of approximately 0.4–1 cm.

In order further to clarify the invention, a description is given below of the use of the insert in the vascular surgical operations heretofore described.

The treatment of a calcified blood vessel (see FIG. 8).

In such an operation, the blood vessel is first constricted on either side of the treatment region, whereupon the blood vessel is cut off at the treatment region. An insert according to FIG. 1 is then selected with a suitable diameter in relation to the blood vessel, a free thread end being pulled out from one end of the insert and fixed at a needle 10 which can be of varying design but is preferably a so-called atraumatic needle, as shown in FIG. 8. The needle with the thread is then inserted into the one part 11 of the blood vessel and the needle together with its associated thread is passed through the wall 12 of the vessel. Then the insert is placed in the part 11 of the blood vessel approximately up to that point where the needle was passed through the vessel wall, approximately half of the insert being inserted in the blood vessel part 11. The second part 13 of the blood vessel is then passed over the remaining, projecting portion of the insert until the ends of the blood vessel parts 11 and 13 meet, as shown in FIG. 8. When this has happened, both of the blood vessel parts 11 and 13 are clamped against the insert by means of surrounding clamping members 14 and 15 at the opposite ends of the insert. Once the clamping members 14 and 15 are in place, the earlier constriction of the blood vessel on either side of the treatment region is removed so that the blood is once again allowed to circulate through the vessel, the blood circulation at the treatment region running through the insert. At this point, it is important that no turbulence occurs in the blood circulation through the insert, for which reason the inner surface of the insert is smooth. Thanks to the above-described preparatory procedure, the treatment region is made accessible for treatment which can be carried out in peace and quiet at the same time as the blood is allowed to circulate unhindered along its earlier path. Once the necessary treatment has been carried out, the ends of the blood vessel parts 11 and 13 are sutured together with a suitable suture material while the insert is still in place and fixed in the blood vessel. Here, a further advantage with the invention is afforded in that the insert functions as a support or substrate during the suturing operation, rather like a darning egg used in the darning of stockings. Once the ends of the blood vessel have been sutured to each other, the clamping members 14 and 15 which have clamped the blood vessel parts 11 and 13 against the insert are released. When the clamping members have been released the blood can circulate both through the interior of the insert and along its outer side, that is to say, between the outer side of the insert and the inner side of the vessel wall 12. Despite the uneven configuration of the outer side of the insert no turbulence will occur in the "outer" blood circulation, since this runs in and is guided by the spiral-shaped groove 5 on the outer side of the insert. By the blood circulation along the outer side of the insert it is possible to test the tightness of the suture, that is to say to ensure that there is no leakage at the joint between the blood vessel parts 11 and 13. Once the tightness of the suture has been established, the insert is removed from its position in the blood vessel. This is effected in that the needle 10 is pulled so that the insert, because of the pulling exercised on it, will part, in the earlier described manner, along the line of fracture or groove 5 to form a thread, which because of the pulling is drawn out through the hole in the vessel wall 12 through which the needle 10 was originally passed. By the use of an atraumatic needle, in which the thread is inserted axially in the thick end of the needle, this hole will be insignificant in size and possible haemorrhage through the hole once the entire insert has been pulled out is negligible.

It will be apparent from the above that the invention entails an advantage in that the blood circulation need be arrested only for a very short time in the initial phase of the operation, whereas the blood circulation need not be arrested during the operation itself and during the final removal of the insert.

The corresponding advantage is obtained in the use of the insert according to the invention for the earlier described so-called de-coking of the carotid artery. In this case, the initial stage of the operation and the treatment proper are carried out in a known manner. Once the treatment proper or de-coking has been carried out, the procedure is, however, carried on in the manner described above. This entails that the arresting of the blood circulation through the carotid artery need only take place once, viz. in the initial stage of the operation; and that the second arresting of the blood circulation in conjunction with the removal of the insert and the suturing of the incision has been eliminated. In view of the fact that the second arresting is normally the longer of the two because of the suturing operation, it will be appreciated that the invention entails considerable advantages. The possibility of the above-described pressure testing of the suture also entails a decided advantage.

In the earlier described operation with the insertion of a graft as a replacement for a missing blood vessel part, the insert according to the invention can replace the earlier discussed support portion which is to be removed once the graft has been permanently united, by healing, to the blood vessel. However, in the use of the insert according to the invention, the procedure is such that a free thread end is passed, in the earlier described manner, through the blood vessel wall and is arranged so that it projects, after the first operational phase or after the major operational phase, a short distance above the skin of the patient at the sutured incision. When the patient later returns to have the insert removed, no new surgical procedure is necessary. Instead, the doctor simply grasps the thread end and pulls it, whereupon the insert parts or breaks up in the above-described manner and is pulled out as a thread. The same is the case for the earlier described operation in ureteritis, that is to say, neither in this case is any new surgical procedure necessary, it being possible to remove the insert by pulling the thread end which, after the original operation, has been left projecting above the skin of the patient.

The invention has been described with reference to particular operational cases, but it will be understood that the invention may also be used in a number of other types of operations in vessels, such as blood vessels, intestines, etc.

What we claim is:

1. An insert for use in vascular surgery comprising an unperforated, hollow body of substantially circular cross-section, said body having a spiral line of fracture extending about the periphery thereof and defining continuous spiral coils to thereby weaken the cohesion of said body along the spiral coils for disassembling said body into an elongated thread.

2. An insert according to claim 1 wherein said body has a smooth inner surface.

3. An insert according to claim 1 wherein said line of fracture is in the form of a groove formed in the outer surface of said body.

4. An insert according to claim 1 wherein the inner surface of said body includes a layer of film-forming binder, and the outer surface thereof includes a spirally-wound thread defining said spiral coils which are embedded in and connected to said film-forming binder, and said spiral line of fracture including a continuous spiral groove formed between said spiral coils.

5. An insert according to claim 4 wherein said spirally-wound thread is of circular cross-section.

6. An insert according to claim 4 wherein the cross-section of said spirally-wound thread is in the form of a segment of a circle having a chord which faces said layer of film-forming binder.

7. An insert according to claim 4 wherein said thread includes a core of metallic material coated with a polymer material.

8. An insert according to claim 1 wherein said body is integrally formed and is homogeneous.

9. An insert according to claim 1 wherein said spiral coils include a spirally-wound thread, said thread including tongues and grooves, the grooves and tongues of juxtaposed coils constructed and arranged to engage each other by snap action, and the portion of said thread facing the inner side of said body being chamfered to provide a smooth inner surface.

10. An insert according to claim 9 wherein said groove is formed integrally with the body of said thread, and said tongues include two jaws formed integrally with the thread of said body, and one of said jaws having a smooth outer surface.

* * * * *